(12) United States Patent
Schlingensiepen et al.

(10) Patent No.: US 8,703,729 B2
(45) Date of Patent: Apr. 22, 2014

(54) MIXTURE COMPRISING AN INHIBITOR OR SUPPRESSOR OF A GENE AND A MOLECULE BINDING TO AN EXPRESSION PRODUCT OF THAT GENE

(75) Inventors: Karl-Hermann Schlingensiepen, Donaustauf (DE); Reimar Schlingensiepen, Regensburg (DE)

(73) Assignee: Biognostik Gesellschaft fur Biomolekulare Diagnostik mbH, Gottingen (DE)

( * ) Notice: Subject to any disclaimer, the term of this patent is extended or adjusted under 35 U.S.C. 154(b) by 720 days.

(21) Appl. No.: 12/382,415

(22) Filed: Mar. 16, 2009

(65) Prior Publication Data

US 2009/0285817 A1 Nov. 19, 2009

Related U.S. Application Data

(62) Division of application No. 10/220,033, filed as application No. PCT/EP01/02694 on Mar. 10, 2001, now abandoned.

(30) Foreign Application Priority Data

Mar. 11, 2000 (EP) .................................. 00105190

(51) Int. Cl.
*C12N 15/113* (2010.01)
*C07H 21/04* (2006.01)

(52) U.S. Cl.
USPC ...................................... 514/44 A; 536/24.5

(58) Field of Classification Search
None
See application file for complete search history.

(56) References Cited

U.S. PATENT DOCUMENTS

| | | | |
|---|---|---|---|
| 5,571,714 | A | 11/1996 | Dasch et al. |
| 5,683,902 | A | 11/1997 | Hampel et al. |
| 5,733,523 | A | 3/1998 | Kuijpers et al. |
| 5,891,858 | A | 4/1999 | Rubenstein |
| 5,958,769 | A | 9/1999 | Roberts et al. |
| 6,248,723 | B1 | 6/2001 | Irvin |
| 6,900,299 | B1 | 5/2005 | Mohapatra et al. |
| 2002/0165174 | A1 | 11/2002 | Gill et al. |

FOREIGN PATENT DOCUMENTS

| | | |
|---|---|---|
| WO | WO 94/25588 | 11/1994 |
| WO | WO 9425588 A2 * | 11/1994 |
| WO | WO 99/50411 | 10/1999 |
| WO | WO 0001410 A1 * | 1/2000 |

OTHER PUBLICATIONS

Hirsch et al, PNAS 1997, vol. 94, pp. 3926-3931.
Opalinska et al. Nature Reviews Drug Discovery, 2002, vol. 1, p. 503-514.

* cited by examiner

*Primary Examiner* — Tracy Vivlemore
(74) *Attorney, Agent, or Firm* — Jacobson Holman PLLC

(57) ABSTRACT

A mixture comprising at least one inhibitor or suppressor of the expression of a gene and at least one molecule binding to an expression product of said gene.

4 Claims, 2 Drawing Sheets

Figure 1:
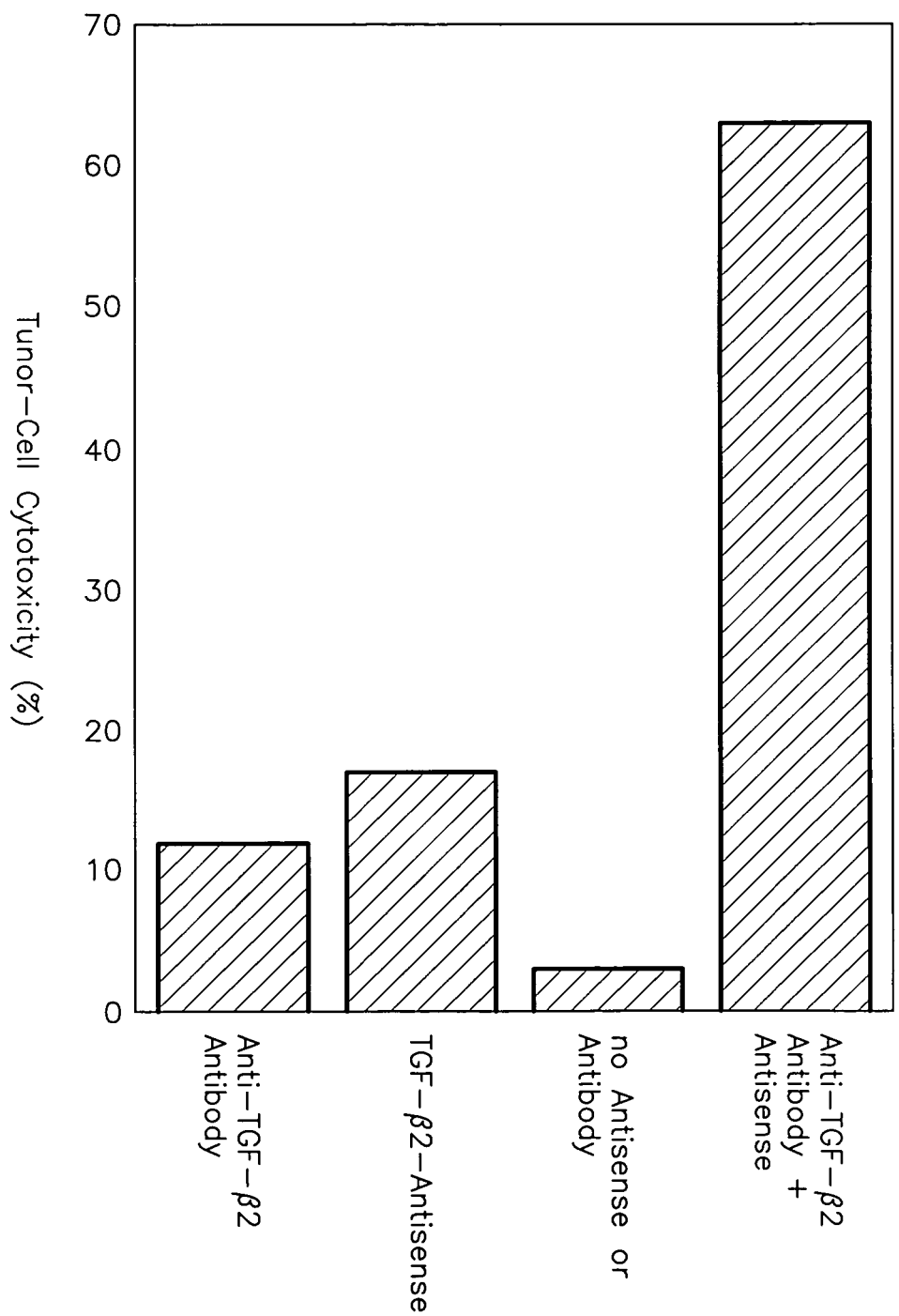

SEQUENCE LISTING

<160> NUMBER OF SEQ ID NOS: 42

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 1
gtagtacacg atgg                                                          14

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 2
ctgatgtgtt gaagaaca                                                      18

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 3
ctctgatgtg ttgaag                                                        16

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 4
cggcatgtct attttgta                                                      18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 5
gctttcacca aattggaagc                                               20

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 6
ctggcttttg ggtt                                                     14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 7
gctgttgact gccc                                                     14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 8
cccagtatta ctgc                                                     14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 9
ggttgaagcc attg                                                     14

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 10
gccgctcaat cttcatc                                                  17

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 11

-continued

```
gaacagttcg tccatg                                                   16

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 12
ccagagtttc ggttc                                                    15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 13
ctaggactgg gacag                                                    15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 14
catcttctgc cattc                                                    15

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 15
cgtaggtggt gctg                                                     14

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 16
gtgttttccc caccag                                                   16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 17
ggttttggtt cactag                                                   16
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 18

Val Pro His Ile Pro Pro Asn
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 19

Met Pro Pro Thr Gln Val Ser
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 20

Gln Met His Pro Trp Pro Pro
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 21

Gln Pro Pro Phe Trp Gln Phe
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 22

Thr Pro Pro Gln Gly Leu Ala
 1               5

<210> SEQ ID NO 23
<211> LENGTH: 7
<212> TYPE: PRT
```

```
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 23

Ile Pro Pro Tyr Asn Thr Leu
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 24

Ala Val Arg Pro Ala Pro Leu
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 25

Gly Ala Lys Pro His Pro Gln
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 26

Gln Gln Leu Ser Pro Leu Pro
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 27

Gly Pro Pro Pro Ser Pro Val
 1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides
```

-continued

```
<400> SEQUENCE: 28

Leu Pro Leu Thr Pro Leu Pro
 1               5

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 29

Gln Leu Asn Val Asn His Gln Ala Arg Ala Asp Gln
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 30

Thr Ser Ala Ser Thr Arg Pro Glu Leu His Tyr Pro
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 31

Thr Phe Leu Pro His Gln Met His Pro Trp Pro Pro
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 32

Val Pro His Ile Pro Pro Asn Ser Met Ala Leu Thr
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 33

Arg Leu Thr Leu Leu Val Leu Ile Met Pro Ala Pro
 1               5                  10
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 34

Arg Lys Leu Pro Pro Arg Pro Arg Arg
  1               5

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 35

Val Leu Ala Ser Gln Ile Ala Thr Thr Pro Ser Pro
  1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 36

Thr Pro Leu Thr Lys Leu Pro Ser Val Asn His Pro
  1               5                  10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 37

Pro Pro Asn Ser Phe Ser Ser Ala Gly Gly Gln Arg Thr
  1               5                  10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 38

Glu Gln Asp Ser Arg Gln Gly Gln Glu Leu Thr Lys Lys Gly Leu
  1               5                  10                  15

<210> SEQ ID NO 39
<211> LENGTH: 13
<212> TYPE: PRT
```

```
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 39

Glu Thr Thr Ile Val Ile Thr Trp Thr Pro Ala Pro Arg
  1               5                  10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 40

Thr Ser Leu Leu Ile Ser Trp Asp Ala Pro Ala Val Thr
  1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: peptide
      obtained by screening randomly synthesized
      peptides

<400> SEQUENCE: 41

Asn Ser Leu Leu Val Ser Trp Gln Pro Pro Arg Ala Arg
  1               5                  10

<210> SEQ ID NO 42
<211> LENGTH: 459
<212> TYPE: DNA
<213> ORGANISM: Artificial Sequence
<220> FEATURE:
<223> OTHER INFORMATION: Description of Artificial Sequence: antisense
      sequence for inhibition of MIA synthesis

<400> SEQUENCE: 42
ggcagggcca gcggtaggct gagctcactg gcagtagaaa tcccatttgt ctgtcttcac    60
atcgactttg ccaggtttca gggtctggtc ctctcggaca atgctactgg ggaaatagcc   120
caggcgagca gccagatctc catagtaatc tccctgaacg ctgcctcccc agaagagccg   180
cccacggccc ttcagcttgg agaagacata caccacttgg ccccggtgaa tggtcaggaa   240
tcggcagtcg ggggccatgt agtcctgaag ggccacagcc atggagatag ggtggctgca   300
ctcctggtcc gcacacagct tccggtcagc cagcttgggc ataggaccac ccctgacacc   360
aggtccggag aaggcagaca gcaagatgat gacaccaagg cacaccaggg accgggccat   420
cgtggactgt gagcaagaga gtgagcaagg gggtgctgg                          459
```

MIXTURE COMPRISING AN INHIBITOR OR SUPPRESSOR OF A GENE AND A MOLECULE BINDING TO AN EXPRESSION PRODUCT OF THAT GENE

This is a divisional of Ser. No. 10/220,033, filed, Oct. 21, 2002, which is a 371 of PCT/EP01/02694, filed Mar. 10, 2001.

Classically, molecules including drugs, used to modulate biological functions through gene products and their derivatives—like e.g. glycosylated, phosphorylated or otherwise modified gene products, have either stimulated or inhibited gene products and/or their derivatives. Stimulation or inhibition was achieved e.g. by use of agonists or antagonists, including small molecular weight molecules, peptides, antibodies etc. Well known examples are H2-antagonists, and β-blockers or antibodies binding to HER2 protein or to immunomodulating receptors as well as hormone receptor binding molecules.

Binding can also be achieved by nucleic acid derivatives like aptamers and spiegelmers.

More recently the inhibition of gene products was also used by inhibiting their expression through antisense, ribozymes, triple helix binders etc. Examples are the inhibition of expression of neurotransmitter receptors in brain or inhibition of cell growth regulating proteins, cytokines and growth factors.

Both approaches, either inhibition of gene products by binding of molecules to the gene products and their derivatives or alternatively inhibition of expression have been used for a large variety of gene products and their derivatives.

The invention pertains to a mixture comprising at least one inhibitor or suppressor of the expression of a gene and at least one molecule binding to an expression product of said gene. The at least one molecule preferably inhibits the functional activity of the expression product.

Surprisingly, this combination shows a supra-additive effect. "Supra-additive" is defined as an effectiveness of a mixture that is at least 20%, preferably more than 50%, more preferably more than 100% better than the sum of the effects of the single compounds of the mixture. This can be tested in any in vitro or in vivo system, which a) expresses the respective gene and b) the expression of the gene has a measurable effect in the system.

Advantages are lower doses and/or higher efficiency compared to each individual approach.

U.S. Pat. No. 5,891,858 (Rubenstein) discloses antisense polynucleotides to human transforming growth factor alpha (TGF-α) and the receptor for human epidermal growth factor (rEGF). It discloses the combination of an antisense polynucleotide for rEGF with antibodies to rEGF (anti-rEGF) but the anti-rEGF is not able to inhibit the activity of the EGF-receptor. In contrast anti-rEGF is a stimulator of the receptor.

Preferably, the at least one inhibitor or suppressor is an nucleic acid molecule or derivative thereof. The at least one nucleic acid molecule is preferably an oligonucleotide, an antisense oligonucleotide and/or a ribozyme inhibiting or interfering with the expression of a gene which plays a role in a patho-physiological event.

Derivatives of gene products are e.g. posttranscritptionally or postranslationally modified gene products e.g. RNA or proteins which have undergone editing or chemical modification e.g. by methylation, phosphorylation, glycosylation etc.

According to the invention it may be useful to integrate the antisense and/or ribozyme molecule into a DNA delivery system. The DNA delivery system comprises viral or non-viral vectors or both and additionally anionic lipids, cationic lipids, non-cationic lipids or mixtures thereof.

Preferably, the antisense and/or ribozyme molecule is modified at one or more of the sugar moieties, the bases and/or the internucleotide linkages, e.g. the phosphate bonds. For example, the modification of the oligonucleotides, ribozymes and/or nucleic acids comprises modifications such as phosphorothioate (S-ODN) internucleotide linkages, methylphosphonate internucleotide linkages, phosphoramidate linkages, peptide linkages, 2'-O-alkyl modifications of the sugar, in particular methyl, ethyl, propyl, butyl and the like, 2'-methoxyethoxy modifications of the sugar and/or modifications of the bases. The various modifications may be combined in an oligo- or polynucleotide.

The antisense and/or ribozyme molecule can also be modified by coupling it to an enhancer of uptake and/or inhibitory activity.

In a further preferred embodiment of the invention, the nucleic acid molecules are coupled to or mixed with folic acid, hormones, steroid hormones such as oestrogene, progesterone, corticosteroids, mineral corticoids, peptides, proteoglycans, glycolipids, phospholipids and derivatives thereof.

In a very preferred embodiment, the nucleic acid molecule is selected from nucleic acid molecules comprising one or more of the following nucleotide sequences:

| | |
|---|---|
| GTA GTA CAC GAT GG | (Seq. ID. No. 1) |
| CTG ATG TGT TGA AGA ACA | (Seq. ID. No. 2) |
| CTC TGA TGT GTT GAA G | (Seq. ID. No. 3) |
| CGG CAT GTC TAT TTT GTA | (Seq. ID. No. 4) |
| GCT TTC ACC AAA TTG GAA GC | (Seq. ID. No. 5) |
| CTG GCT TTT GGG TT | (Seq. ID. No. 6) |
| GCT GTT GAC TGC CC | (Seq. ID. No. 7) |
| CCC AGT ATT ACT GC | (Seq. ID. No. 8) |
| GGT TGA AGC CAT TG | (Seq. ID. No. 9) |
| GCC GCT CAA TCT TCA TC | (Seq. ID. No. 10) |
| GAA CAG TTC GTC CAT G | (Seq. ID. No. 11) |
| CCA GAG TTT CGG TTC | (Seq. ID. No. 12) |
| CTA GGA CTG GGA CAG | (Seq. ID. No. 13) |
| CAT CTT CTG CCA TTC | (Seq. ID. No. 14) |
| CGT AGG TGG TGC TG | (Seq. ID. No. 15) |
| GTG TTT TCC CAC CAG | (Seq. ID. No. 16) |
| GGT TTT GGT TCA CTA G | (Seq. ID. No. 17) |

Further suitable nucleic acid sequences are known to those skilled in the art. More sequences and methods for selecting such sequences can be found for example in WO 94/25588 or WO 98/33904.

In a further embodiment, the inhibitor or suppressor is a peptide, protein and/or low molecular weight substance, which is able to bind to DNA or RNA coding for the gene, thus inhibiting or suppressing expression of the gene. Suitable proteins also comprise antibodies and antibody fragments.

The mixture of the invention comprises preferably as the at least one molecule binding to the expression product of the gene an antibody, antibody fragment, such as a $F_{ab}$ fragment, single chain antibody or combinations thereof. The antibody, antibody fragment, such as a $F_{ab}$ fragment, single chain antibody or combinations thereof are e.g. obtainable by screening of antibody libraries and testing the expression products for binding to an expression product of the gene.

In a further embodiment the at least one molecule binding to an expression product of the gene is preferably a peptide and/or protein. The peptide and/or protein is e.g. obtainable by screening an expression library and testing the expression products for binding to an expression product of the gene.

The synthetic peptide and/or protein may also be obtained by screening randomly synthesised peptides and/or polypeptides for binding to an expression product of the gene. Peptides binding to expression products are for example disclosed in EMBO J. 20 (2001) 340-349. The peptides bind to MIA (Melanoma Inhibitory Activity), thus inhibiting the functional activity of MIA. Suitable peptides (SEQ ID No. 18-41) are for example
VPHIPPN
MPPTQVS
QMHPWPP
QPPFWQF
TPPQGLA
IPPYNTL
AVRPAPL
GAKPHPQ
QQLSPLP
GPPPSPV
LPLTPLP
QLNVNHQARADQ
TSASTRPELHYP
TFLPHQMHPWPP
VPHIPPNSMALT
RLTLLVLIMPAP
RKLPPRPRR
VLASQIATTPSP
TPLTKLPSVNHP
PPNSFSSAGGQRT
EQDSRQGQELTKKGL
ETTIVITWTPAPR
TSLLISWDAPAVT
NSLLVSWQPPRAR In another embodiment, the mixture of the invention comprises a low molecular weight molecule binding to an expression product of the gene. In particular, the low molecular weight molecule is obtainable by using combinatorial chemistry and testing the products for binding to an expression product of the gene.

Low molecular weight molecules (small molecules) as used herein are molecules having up to 100 carbon atoms in combination with further atoms such as N, S, O, P and the like. Suitable compounds binding to an expression product can be found in FIG. 2, all binding to MIA.

The molecule or factor binding to an expression product of the gene may also be DNA or RNA molecule or a derivative thereof including aptamers and/or spiegelmers that bind to the expression product to the gene.

In a preferred embodiment of the invention, the gene is selected from the group consisting of TGF-β, erbB-2, MIA, c-jun, junB, c-fos, VCAM, NF-kappaB p65, NF-kappa B p50, ICAM, VEGF and NF-kB 2.

The invention pertains as well to oligonucleotides having the sequences Seq. ID. No 1 to 17.

A medicament comprising the mixture of the invention is also subject matter of the present invention.

The invention further concerns a method of using a mixture comprising at least one suppressor or inhibitor of the expression of a gene and at least one molecule or factor binding to an expression product of said gene for treating tumors, immune disorders, or improving organ or cell transplantation, including transplantation of hematoietic stem cells and their derivatives including erythrocytes, white blood cells, platelets, thrombocytes and their precursor cells. Organ transplantation includes transplantation of liver, kidney, heart, lung, gastrointestinal organs, bone, pancreas, cartilage, neurones, islet cells and stem cells from which these organs can be derived or reconstructed.

The invention furthermore pertains to a method of treating tumors, immune disorders, or improving organ or cell transplantation by administration of an effective amount of a combination of at least one molecule or factor suppressing or inhibiting an expression of a gene and at least one factor binding to an expression product of said gene whereby inhibition of tumor growth, improvement of organ or cell transplantation, enhancement or inhibition of immune response is enhanced in a supra-additive manner, including transplantation of hematoietic stem cells and their derivatives including erythrocytes, white blood cells, platelets, thrombocytes and their precursor cells. Organ transplantation includes transplantation of liver, kidney, heart, lung, gastrointestinal organs, bone, pancreas, cartilage, neurones, islet cells and stem cells from which these organs can be derived or reconstructed.

The mixture of the present invention is also useful in Drug Target Validation, i.e. to identify genes that are relevant for a certain pathological state by testing the effect of the mixture of the present invention on a cell system or organism.

In a further embodiment the invention is directed to a method for reducing a functional activity of a gene product in a biological system comprising treatment of the biological system simultaneously or successively with at least one inhibitor or suppressor of the expression of a gene and at least one molecule inhibiting functional activity of an expression product of said gene. The biological system may be a cell, a cell culture, an organ or an organism.

FIG. 1 shows a strongly supra-additive effect of a combination of both the blocking of a gene with an antisense molecule combined with a neutralising antibody.

Figure 2:
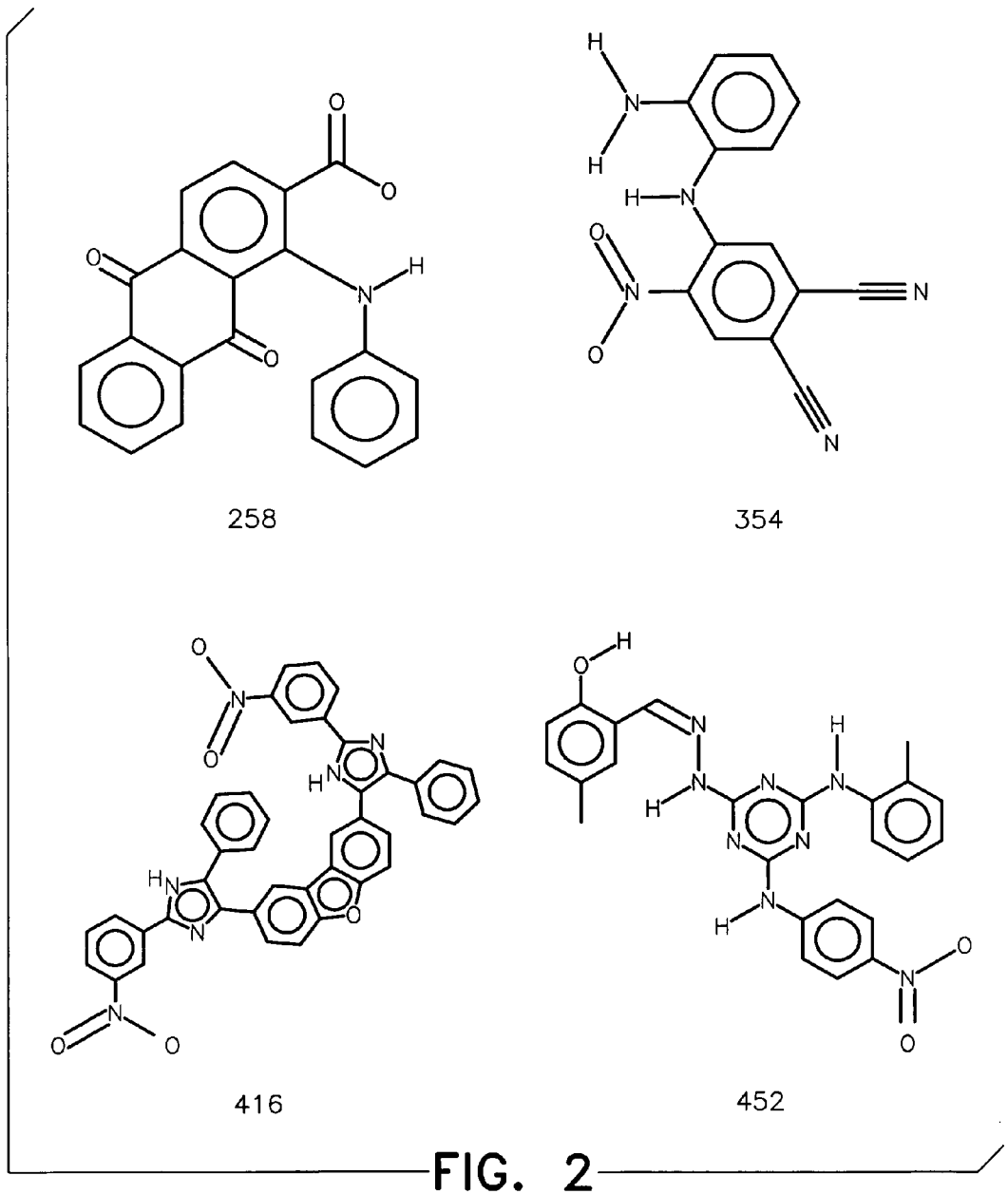

FIG. 2 discloses small molecules able to inhibit the gene product MIA.

EXAMPLES

Example 1

To study the effects of neutralising antibody against TGF-β2 as an inhibitor of the gene product, antisense oligonucleotides against TGF-β2 as an inhibitor of gene expression and a combination of the two, upon immune response activity of cytotoxic T-lymphocytes (CTL) and Lymphokine activated killer cells (LAK cells) on tumor cells, a CARE-LASS assay has been employed (Lichtenfels, R., Biddison, W. E. 1 Schulz, H. 1 Voyt, A. B. and R. Martin. CARE-LASS (calcein-release assay), an improved fluorescence based test system to measure cytotoxic lymphocyte activity. J. Immunol. Meth., 172: 227-239, 1994).

Generation of LAK Cells and CTLs

Peripheral blood mononuclear cells (PBMC) were isolated from venous blood of healthy donors by standard Ficoll-Hypaque gradient centrifugation, as described previously. Briefly, heparinized blood was mixed with equal volumes of complete medium (RMPI 1640 medium supplemented with 10% (v/v) fetal calf serum and 1 mM L-Glutamine) and layered onto Ficoll-Hypaque (Pharmacia, Uppsala, Sweden) gradients. After centrifugation at 400 g for 30 min at room temperature, PBMCs banded at the plasma-Ficoll interface were removed, washed tree times and resuspended in complete medium. Cell viability, as determined by Trypan blue exclusion, was >97%. Lymphocytes were activated by treatment with 10 U/ml IL-1 alpha and 100 U/ml IL-2.

At the day of the assay, glioma tumor cells were harvested, washed twice in 50% FCS/PBS solution and resuspended at 10 Mio cells/ml in 5% FCS/PBS. Calcein-AM (Molecular Probes, USA) was added to a final concentration of 25 µM. The cells were labelled for 30 min at 37° C. then washed twice in 5% FCS/PBS, adjusted to 1 Mio cells/ml and loaded into 96-well U-shaped microtiter plates at the final concentration of 0.1 Mio/100 µL/1 well (Nunc, Denmark).
Either
    antisense phosphorothioate TGF-β2 oligonucleotides (f.c. 2-5 µM),
or
    neutralising antibody against TGF-β2 (f.c. 100 mg/ml)
or
    a combination of the two
or
    neither of the two were added as indicated in the Figure.

Measure of cytotoxic activity of effector cells (E) on the target cells (T):

To measure cytotoxic activity of effector cells, wells were loaded with 100 µM of CTL and LAK cells (E) to produce the desired E:T ratios of 1:20.

Spontaneous Release of Calcein

To measure spontaneous release and total release of calcein, wells were preloaded with 100 µl 50% FCS/PBS or 100 µL lysis buffer (50 nM sodium borate, 0.10% Triton x 100, pH 9.0) respectively. After incubating the plate for 4 h at 37° C. the supernatants (50 µL) were transferred into new wells and measured using an automated fluorescence scanner (Titertek Fluoroskan II, Germany). The cytotoxicity was determined from the following equation:

$$\frac{F/CTL \text{ assay} - F \text{ spontaneous release}}{F \text{ total lysis} - F \text{ spontanous release}} \times 100 = \% \text{ cytotoxicity}$$

Example 2

Hematopoietic Stem cells were collected by apheresis after mobilisation from bone marrow with a daily dose of 10 µg/kg/day of rhG-CSF for 5 days or from cord blood (cord blood stem cells) and enrichment of CD34+ cells achieved with immunopurification.

The multipotent progenitor fraction of both, bone marrow derived and cord blood derived stem cells, are of critical relevance for clinical application. A problem of current stem cell transplantation is the low number of stem cells generated by optimised cytokine cocktails. Furthermore a critical problem for long term success is the quiescence and maturation of multipotent progenitor fraction by current treatment with cytokine cocktails.

Both the number of cells and the proliferative capacity of bone marrow stem cells can be improved by treatment with TGF-β1 inactivating antibodies or with TGF-β1 antisense oligonucleotides.

Surprisingly a combination of both, TGF-β1 inactivating antibodies and TGF-β1 antisense oligonucleotides had a strongly supra-additive effect.

Bone marrow derived and cord blood derived stem cells were treated with either
    antisense TGF-β1 oligonucleotides.
or
    neutralising antibody against TGF-β1
or
    a combination of the two
or
    neither of the two (controls).

The number of multipotent proliferating progenitor cells was increased by 85% through treatment with TGF-β1 antisense oligonucleotides compared to controls.

The number of multipotent proliferating progenitor cells was increased by 63% through treatment with TGF-β1 neutralising antibody compared to controls.

The number of multipotent proliferating progenitor cells was increased by more than 350% through treatment with a combination of both, TGF-β1 inactivating antibodies and TGF-β1 antisense oligonucleotides compared to controls.

Example 3

A combination of both, TGF-β1 binding peptide and TGF-β1 antisense oligonucleotides had a similarly strongly supra-additive effect on the proliferation of multipotent proliferating hematopoietic progenitor cells.

The number of multipotent proliferating progenitor cells was increased by 85% through treatment with TGF-β1 antisense oligonucleotides compared to controls.

The number of multipotent proliferating progenitor cells was increased by 57% through treatment with TGF-≈1 binding peptide compared to controls.

The number of multipotent proliferating progenitor cells was increased by more than 3-fold through treatment with a combination of both, TGF-β1 binding peptide and TGF-β1 antisense oligonucleotides compared to controls.

Example 4

The c-erbB-2 gene (also called p185, HER-2 or neu) is amplified and/or overexpressed in 30-45% of human mammary carcinomas, and in up to 50% in pancreas carcinomas, ovarian cancer, gastric carcinomas, non-small-cell lung cancer, oral squamous cell carcinomas.

An inactivating antibody for cerbB-2 or HER2 with the trade name Herceptin® has been used for treatment of breast cancer patients. Clinical studies initially showed good therapeutic potential, while current clinical studies give controversial results. We found that a combination of an inhibitor of cerbB-2 gene expression with a molecule binding to the cerbB-2 gene product strongly enhanced the effect of each molecule alone.

Ovarian carcinoma cells and pancreas carcinoma cells were treated either with either
    antisense c-erbB-2 oligonucleotides,
or
    neutralising antibody against c-erbB-2
or
    a combination of the two
or
    neither of the two.

Inhibition of tumor cell proliferation was between 18% and 31% with antisense c-erbB-2 oligonucleotides, between 13 and 340% with antibodies, but by more than 85% with a combination of the two.

Example 5

Inhibition of endogenous MIA synthesis by a transfecting vector expressing the antisense sequence:

(SEQ ID NO: 42)
GGCAGGGCCAGCGGTAGGCTGAGCTCACTGGCAGTAGAAATCCCATTTGT

CTGTCTTCACATCGACTTTGCCAGGTTTCAGGGTCTGGTCCTCTCGGACA

ATGCTACTGGGGAAATAGCCCAGGCGAGCAGCCAGATCTCCATAGTAATC

TCCCTGAACGCTGCCTCCCCAGAAGAGCCGCCCACGGCCCTTCAGCTTGG

AGAAGACATACACCACTTGGCCCCGGTGAATGGTCAGGAATCGGCAGTCG

GGGGCCATGTAGTCCTGAAGGGCCACAGCCATGGAGATAGGGTGGCTGCA

CTCCTGGTCCGCACACAGCTTCCGGTCAGCCAGCTTGGGCATAGGACCAC

CCCTGACACCAGGTCCGGAGAAGGCAGACAGCAAGATGATGACACCAAGG

CACACCAGGGACCGGGCCATCGTGGACTGTGAGCAAGAGAGTGAGCAAGG

GGGTGCTGG or parts of this sequence in human, MIA-secreting melanoma as well as breast cancer cell lines reduced their migration activity, as well as increasing their adhesion to matrices, both suggesting a strong inhibitory effect of MIA inhibitors and tumor invasion and metastasis.

Supra-additive effects were achieved with a combination of a MIA binding peptide with a transfecting vector expressing the above antisense sequence on reduction of their migration activity, as well as increasing their adhesion to matrices.

Example 6

Supra-additive inhibition can also be achieved by combining a transcription factor or its binding domain, binding to a regulatory sequence of receptors, enzymes, transcription factors, cell adhesion molecules, cytokines or growth factors, such as TGF-β, MIA, VCAM, ICAM, c-jun, junB, NF-kappaB, VEGF or integrins genes with a molecule of small molecular weight, e.g. derived by combinatorial chemistry, binding to receptors, enzymes, transcription factors, cell adhesion molecules, cytokines or growth factors, such as TGF-β, MIA, VCAM, ICAM, c-jun, junB, NF-kappaB, VEGF or integrins.

Example 7

Supra-additive inhibition can also be achieved by combining a peptide or a protein, binding to the mRNAs transcribed from receptors, enzymes, transcription factors, cell adhesion molecules, cytokines, or growth factors, such as TGF-β, MIA, VCAM, ICAM, c-jun, junB, NF-kappaB, VEGF or integrin genes with a small molecule binding to receptors, enzymes, transcription factors, cell adhesion molecules, cytokines, or growth factors, such as TGF-β, MIA, VCAM, ICAM, c-jun, junB, NF-kappaB, VEGF or integrins.

Example 8

Supra-additive inhibition can also be achieved by combining peptide, a protein e.g. a transcription factor or its binding domain, binding to a regulatory sequence of receptors, enzymes, transcription factors, cell adhesion molecules, cytokines growth factors, such as TGF-β, MIA, VCAM, ICAM, c-jun, junB, NF-kappaB, VEGF or integrin genes with a Spiegelmer binding to receptors, enzymes, transcription factors, cell adhesion molecules, cytokines growth factors, such as TGF-β, MIA, VCAM, ICAM, c-jun, junB, NF-kappaB, VEGF or integrins.

Example 9

Supra-additive inhibition can also be achieved by combining a transcription factor or its binding domain, binding to a regulatory sequence of receptors, enzymes, transcription factors, cell adhesion molecules, cytokines or growth factors, such as TGF-β, MIA, VCAM, ICAM, c-jun, junB, NF-kappaB, VEGF or integrin genes with peptides binding to receptors, enzymes, transcription factors, cell adhesion molecules, cytokines or growth factors, such as TGF-β, MIA, VCAM, ICAM, c-jun, junB, NF-kappaB, VEGF or integrins.

The mixtures of examples 6 to 9 are especially useful for neuronal stem cell expansion.

Example 10

Supra-additive effects can also be achieved by combining an inhibitor of c-jun expression with a molecule binding the c-jun gene product or derivative thereof. Such mixtures are useful for the protection of neurones to ischaemia, hypoxia, degeneration or overstimulation.

Example 11

HPP-Q-Assay

The effect of the combination of antisense-TGF-β1-oligonucleotide and anti-TGF-β1-antibody on human hematopoietic Stern cells was investigated. For this reason, purified human CD34-positive cells from peripheral blood were first cultured for 72 h in medium containing cytokines (IL-3, IL-6, GM-CSF, G-CSF, SCF) without oligonucleotides or in the presence of antisense TGF-β1 oligonucleotides or a missense control. Subsequently, in an HPP-Q-assay (high proliferative potential quiescent cell-assay) the cells were further cultivated with or without anti-TGF-β1 antibody.

The HPP-Q-assay compares cells cultivated in a control medium including cytokines (IL-3, IL-6, IL-11, G-CSF, GM-CSF, SCF and Epo) with cells cultured in the same cytokine-containing medium in the presence of anti-TGF-β1-blocking antibody. The control reveals cytokine-responsive progenitors, while the addition of blocking TGF-β-antibody induces quiescent progenitors.

The HPP-Q-assay was performed as described by the manufacturer (StemBio Research, Villejuif, France). Briefly $1.6 \times 10^4$ cultured cells were plated in triplicate for each medium in 1 ml aliquots into 35-mm tissue dishes. After 18 days the number of colonies (CFU=most immature cells gained) was counted.

Table 1 shows that antisense TGF-β1 increases the effect of the anti-TGF-β1 antibody (TGF-β1 AB) on CD34-positive cells from a lymphoma patient more than twofold, i.e. in the presence of antisense TGF-β1 the cell number more than doubles compared to antibody alone.

|  | CFU colony number |
|---|---|
| Control + TGF-β1 AB | 17.66 ± 2.49 |
| Antisense TGF-β1 + TGF-β1 AB | 41.33 ± 2.49 |

Table 2 shows that also antibody amplifies the effect of antisense TGF-β1 on CD34-positive cells from two lymphoma and one myeloma patient: The cell number gained with antisense-TGF-61 alone increases almost threefold if TGF-β1 antibody is added as well.

|  | CFU colony number | |
|---|---|---|
|  | Antisense-TGF-β1 | Antisense-TGF-β1 + TGF-β1 AB |
| Lymphoma 1 | 19.00 ± 1.41 | 37.00 ± 6.48 |
| Lymphoma 2 | 24.00 ± 2.34 | 63.33 ± 5.31 |
| Myeloma | 23.33 ± 5.13 | 60.00 ± 3.45 |

Thus, the combination of antisense TGF-β1 and anti-TGF-β1 antibody results in a more than twofold increase in cell number compared to antisense or antibody alone.

The invention claimed is:

1. A method of treating a tumor comprising administering to a patient in need thereof a mixture comprising (a) at least one oligonucleotide selected from the group consisting of SEQ ID NOS: 1 to 17, modified or unmodified, for inhibiting or suppressing expression of TGF-beta, and (b) at least one antibody or antibody fragment, for inhibiting functional activity of a protein expression product of TGF-beta.

2. The method of claim 1 wherein the oligonucleotide is integrated into a viral or non-viral vector together with a lipid selected from the group consisting of anionic lipids, cationic lipids, non-cationic lipids, and mixtures thereof.

3. The method of claim 2 wherein the oligonucleotide is an antisense oligonucleotide modified (a) at one or more sugar moieties, bases, and internucleotide linkages and/or (b) by coupling the antisense oligonucleotide to an enhancer of uptake and/or inhibitory activity.

4. The method of claim 1 wherein the antibody fragment is a Fab fragment, single chain antibody, or a combination thereof.

\* \* \* \* \*